US009610297B2

(12) United States Patent
Heep et al.

(10) Patent No.: US 9,610,297 B2
(45) Date of Patent: Apr. 4, 2017

(54) STABILIZATION OF VITAMIN $B_{12}$

(71) Applicant: Bayer Intellectual Property GMBH, Monheim (DE)

(72) Inventors: Iris Heep, Cologne (DE); Hans-Rolf Taterra, Odenthal (DE)

(73) Assignee: Bayer Intellectual Property GmbH (DE)

( * ) Notice: Subject to any disclaimer, the term of this patent is extended or adjusted under 35 U.S.C. 154(b) by 0 days.

(21) Appl. No.: 14/808,425

(22) Filed: Jul. 24, 2015

(65) Prior Publication Data
US 2015/0328318 A1 Nov. 19, 2015

Related U.S. Application Data

(62) Division of application No. 12/951,581, filed on Nov. 22, 2010, now Pat. No. 9,089,582, which is a division of application No. 12/045,831, filed on Mar. 11, 2008, now abandoned.

(30) Foreign Application Priority Data

Mar. 16, 2007 (DE) ........................ 10 2007 012 644

(51) Int. Cl.
*A61K 31/662* (2006.01)
*A61K 31/714* (2006.01)
*A61K 9/08* (2006.01)
*A61K 47/10* (2006.01)
*A61K 31/66* (2006.01)
*A61K 9/00* (2006.01)

(52) U.S. Cl.
CPC ............ *A61K 31/66* (2013.01); *A61K 9/0019* (2013.01); *A61K 31/662* (2013.01); *A61K 31/714* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 2,566,123 A | 8/1951 | De Rose | |
| 2,579,679 A | 12/1951 | Leffler | |
| 2,662,048 A | 12/1953 | Winsten | |
| 2,748,054 A | 5/1956 | Jurist | |
| 2,778,771 A | 1/1957 | Michel et al. | |
| 2,939,821 A | 6/1960 | Freedman et al. | |
| 4,234,206 A | 11/1980 | Hofbauer et al. | |
| 4,469,684 A | 9/1984 | Huggins et al. | |
| 5,014,927 A | 5/1991 | Ogawa et al. | |
| 5,080,908 A | 1/1992 | Ono et al. | |
| 5,976,555 A | 11/1999 | Liu et al. | |
| 2003/0229056 A1 | 12/2003 | Bertha | |
| 2004/0153946 A1 | 8/2004 | Tsuchinaga | |
| 2005/0074443 A1 | 4/2005 | Treadwell | |
| 2005/0232981 A1 | 10/2005 | Ben-Sasson | |
| 2006/0120967 A1 | 6/2006 | Namburi et al. | |
| 2008/0039422 A1 | 2/2008 | Cruz et al. | |

FOREIGN PATENT DOCUMENTS

| | | |
|---|---|---|
| BE | 576619 A1 | 7/1959 |
| DE | 951162 C | 10/1956 |
| DE | 2522187 B1 | 10/1976 |
| DE | 3337304 A1 | 5/1984 |
| ES | 247522 A1 | 6/1959 |
| FR | 1263794 A | 6/1961 |
| FR | 1285213 A | 2/1962 |
| GB | 692968 | 6/1953 |
| GB | 806714 | 12/1958 |
| GB | 822127 A | 10/1959 |
| GB | 902377 A | 8/1962 |
| HU | 150885 | 7/1962 |
| JP | 41-007474 B4 | 4/1966 |
| JP | S55-49313 A | 4/1980 |
| JP | 63313736 A | 12/1988 |
| JP | 2311417 A | 12/1990 |
| JP | 4049239 A | 2/1992 |
| JP | 04-235925 | 8/1992 |
| JP | H05-124967 A | 5/1993 |
| JP | S39-11864 B | 8/1993 |
| JP | 2000319186 A | 11/2000 |
| JP | 2001048780 A | 2/2001 |
| JP | 02145521 A | 5/2002 |
| JP | 2005015368 A | 1/2005 |
| JP | 2005247800 A | 9/2005 |
| JP | 2006124286 A | 5/2006 |
| WO | 97/31620 A2 | 9/1997 |
| WO | 2005002589 A1 | 1/2005 |
| WO | 2005094842 A1 | 10/2005 |

OTHER PUBLICATIONS

Bayer, Safety Data Sheet, Coforta 100 Injectable Phosphorous Solution, Creation Date: Jun. 25, 2003.*
Nuntaprasert, A., "The field effect of Catosal on the acute phase response, performance and metabolic disorders of farrowing sows in Thailand", Proceedings of the 19th IPVS Congress 2006, Copenhagen, vol. 2, p. 487.*
Rosenthal, H.L., et al., "The Determination of Vitamin B12 Activity in Human Serum," 1952, J Biol Chem, pp. 433-442.
Froyman et al., machine translation of WO 2005/002589, published 2005, pp. 1-3.
"Butyl Alcohols," Chemical Encyclopedia, Great Russian Encyclopedia, Moscow 1998, 1:336-337, col. 650, with translation, 4 pages.
Committee for Veterinary Medicinal Products, Benzyl Alcohol, Summary Report, 1997, The European Agency for the Evaluation of Medicinal Products Veterinary Medicines Evaluation Unit.
Merriam-Webster OnLine Dictionary "Derivative", also available at http://www.meriam-webster.com/dictionary/derivative; last viewed Jul. 2009.
English Language Abstract, JP43-010862, 1 page.
English Language Translation, JP45-011919.
English Language Translation, JP46-15320.
International Search Report issued Sep. 18, 2008 in PCT/EP2008/001819, 4 pages.

* cited by examiner

*Primary Examiner* — Layla Berry
*Assistant Examiner* — Bahar Craigo
(74) *Attorney, Agent, or Firm* — Senniger Powers LLP

(57) ABSTRACT

The invention relates to preparations comprising vitamin $B_{12}$ and a butanol, and to the use of butanol for stabilizing vitamins.

18 Claims, 1 Drawing Sheet

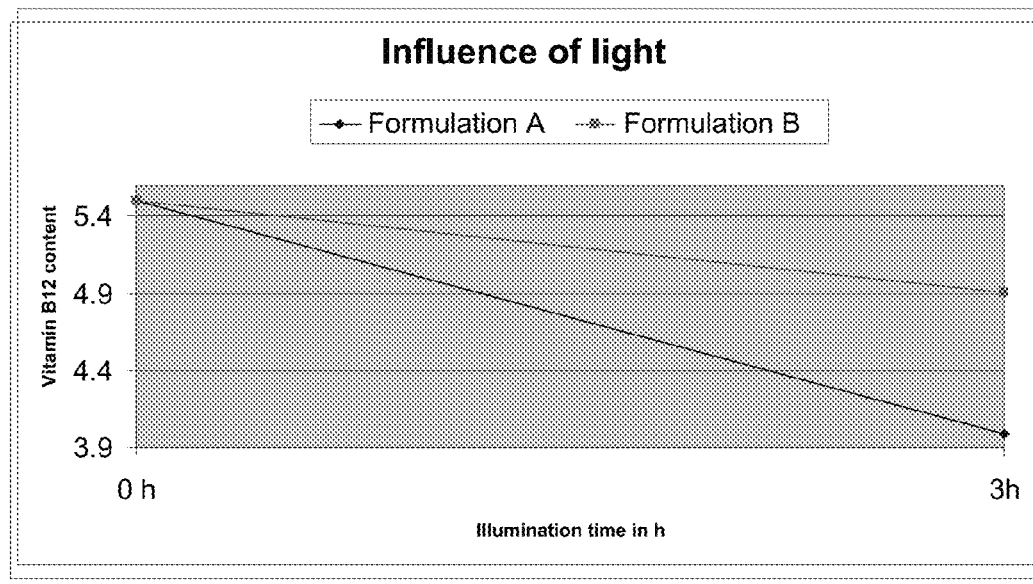

STABILIZATION OF VITAMIN $B_{12}$

REFERENCE TO RELATED APPLICATIONS

This application is a division of U.S. patent application Ser. No. 12/951,581, filed Nov. 22, 2010, which is a division of U.S. patent application Ser. No. 12/045,831, filed Mar. 11, 2008, now abandoned, and claims priority to German Application No. DE 102007012644.3, filed Mar. 16, 2007, the entire disclosures of which are incorporated herein by reference.

FIELD OF THE INVENTION

The invention relates to preparations comprising vitamin $B_{12}$ and a butanol, and to the use of butanol for stabilizing vitamins.

BACKGROUND OF THE INVENTION

It is generally known that vitamins are not very stable and degradation is to be observed for example on storage. This also applies to the so-called B vitamins, explicitly vitamin $B_{12}$. For this reason, there have been very many studies on the topic of the stabilization of vitamins and of vitamin $B_{12}$. A simple solution to this problem is for example separating the vitamin $B_{12}$ from substances which promote its degradation. Thus, for example, JP200612486 describes 3 partial solutions in which individual partial formulations are present. Vitamin $B_{12}$ is stabilized not only in liquid formulations, but also in tablets or granules, as described for example in EP416773. Most of the studies on the stabilization of vitamin $B_{12}$ relate however to liquid formulations. Such solutions can also be used to fill capsules (FR1472901), or the solutions are freeze dried for further stabilization (JP63313736). Among the vitamin $B_{12}$ solutions ready for use there are some stabilized by the addition of iron salts (FR1285213, GB902377). The solutions may likewise comprise EDTA (ethylenediaminetetraacetic acid, U.S. Pat. No. 2,939,821 or GB822127). Alkali metal salts or alkaline earth metal salts are also said to have a stabilizing effect on vitamin $B_{12}$ (U.S. Pat. No. 2,566,123). Vitamins can also take place by use of amino acids (U.S. Pat. No. 2,748,054) or by cyclodextrins (JP4049239), as well as by ammonium sulphate (U.S. Pat. No. 2,778,771), by sodium iodide (JP41007474), potassium cyanide (GB692968), maleic acid (JP64011864), thiopropionic acid (U.S. Pat. No. 2,579,679), gluconolactone (ES247522), lecithins (JP55049313), urea (JP43010862) or else by fatty acid esters with cysteine (U.S. Pat. No. 2,662,048) or by antioxidants (DE25222187) and so-called chelating agents (WO97/31620). Even solutions in N-methylpyrrolidone DE3337304 are described, in which vitamin $B_{12}$ is said to be stable. In some studies, vitamin $B_{12}$ is stabilized through the use of polyvalent alcohols (JP2311417, JP63313736, JP05124967, FR1263794, JP04-235925, JP2000-319186 or HU150885). The use of alcohols for stabilizing vitamin $B_{12}$ is proposed generally in JP2005247800, WO2005/094842, WO02/02145, BE576619 or JP02145521. US2005074443 describes long-chain alcohols for stabilizing vitamin $B_{12}$. However, vitamin $B_{12}$ itself is also used in turn to stabilize other substances (JP2001-048780, JP2005-015368).

Thus, in JP46-15320 propylene glycol is employed for isotonicity and benzyl alcohol as analgesic. The actual stabilization is achieved by dextran and gelatin (hydrophilic macromolecules). In JP45-011919, the alcohols propylene glycol, benzyl alcohol, mannitol or glycerol are described for stabilizing 5,6-dimethylbenzimidazolyl cobamide coenzyme.

A possible way of stabilizing vitamin $B_{12}$ through the use of butanol has been found. Although JP2005247800 mentions alcohols for stabilizing vitamin $B_{12}$, for example the chlorobutanol contained therein is unsuitable specifically for the solution used in this case and is, on the contrary, harmful. Likewise, the benzyl alcohol contained in JP46-15320 or JP45-011919 is distinctly disadvantageous for the formulation described herein, because benzyl alcohol cannot be metabolized by all animals (EMEA, Committee for veterinary medicinal products, summary report, benzyl alcohol, 1997) and formulations with benzyl alcohol therefore cannot be employed as widely as formulations with butanol.

SUMMARY OF THE INVENTION

The invention relates to:
A preparation comprising vitamin $B_{12}$ and butanol.
The use of such a preparation for the manufacture of a medicament.
The use of butanol for stabilizing vitamin $B_{12}$.
The use of butanol for producing preparations of vitamin $B_{12}$ with improved vitamin $B_{12}$ stability.

BRIEF DESCRIPTION OF THE DRAWINGS

FIG. 1 is a comparison of the photostabilities of a formulation without n-butanol (A) with a formulation with n-butanol (B), according to Example 1.

DESCRIPTION OF THE PREFERRED EMBODIMENTS

Vitamin $B_{12}$ in the narrower sense frequently means cyanocobalamin, but there are also other compounds which are likewise covered by the generic term vitamin $B_{12}$; these are also referred to as cobalamins. It is intended herein that the term vitamin $B_{12}$ generally means all compounds which act as coenzyme in the human and/or animal body or can be converted into the corresponding coenzyme forms. These vitamin $B_{12}$ compounds have in common the Corrin structure with a trivalent cobalt as central atom and with a 5,5-dimethylbenzimidazole residue which is alpha-glycosidically linked via D-ribofuranose 3-phosphate. Most cobalamins differ from one another merely in one axial substituent. Examples of compounds which can be employed as vitamin $B_{12}$ are: cyanocobalamin (axial substituent=CN), aquocobalamin ($B_{12a}$, axial substituent=—$O^+H_2$), hydroxocobalamin ($B_{12b}$, axial substituent=—OH), nitritocobalamin ($B_{12c}$; axial substituent=—$NO_2$); 5'-deoxyadenosylcobalamin (coenzyme $B_{12}$, axial substituent=5'-deoxyadenosyl) and methylcobalamin (methyl $B_{12}$, axial substituent=—$CH_3$). Adenosylcobalamin and methylcobalamin are the real active forms (coenzyme forms), and aquocobalamin and hydroxocobalamin are storage forms which likewise occur in the body.

According to a preferred embodiment, the preparations according to the invention additionally comprise a pharmacologically acceptable phosphonic acid derivative. Pharmacologically acceptable phosphonic acid derivatives which can be employed according to the invention are normally organic compounds which are suitable as metabolic stimulants and tonics in particular for productive and domestic animals. Preferred examples which may be mentioned are the compounds butaphosphan and toldimfos which have been known for a long time and are used inter alia for mineral supplementation (phosphorus).

Butaphosphan has the chemical name (1-butylamino-1-methyl)ethylphosphonic acid and has the structural formula

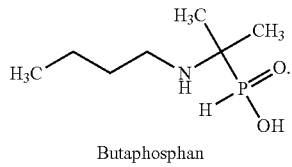

Butaphosphan

Butaphosphan is normally employed as free acid.

Toldimfos has the chemical name (4-dimethylamino-o-tolyl)phosphonic acid and has the following structural formula

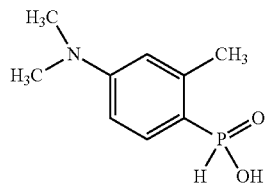

Toldimfos

Toldimfos is normally employed as sodium salt.

The present invention encompasses both the use of the free active ingredients and of their pharmaceutically acceptable salts, and the use of the corresponding hydrates and solvates of the compounds or their salts.

Vitamin $B_{12}$ is typically employed in the medicaments according to the invention in a proportion of from 0.00001 to 0.1%, preferably 0.0001 to 0.05% and particularly preferably from 0.001 to 0.01%. Here and hereinafter—unless indicated otherwise—the percentage data mean percent (M/V). This means: mass of the relevant substance in grams per 100 ml of finished solution.

Butanol refers to isomeric aliphatic alcohols which have an alkyl chain with four carbon atoms; they may be linear or branched, specifically as n-butanol, sec-butanol, tert-butanol and isobutanol. Isobutanol and n-butanol are preferred, and especially n-butanol.

Butanol is normally employed in concentrations of from 0.1 to 10%, preferably from 0.5 to 7% and particularly preferably from 1 to 5%. The percentage data mean % (M/V).

The pharmacologically active phosphonic acids, such as, for example, toldimfos or, in particular, butaphosphan, are employed in the medicaments according to the invention in a proportion of from 0.1 to 40%, preferably 1 to 30% and particularly preferably 5 to 20%.

The preparations according to the invention are preferably liquid and normally comprise water or a water-miscible substance as solvent. Examples which may be mentioned are glycerol, propylene glycol, polyethylene glycols, tolerated alcohols such as ethanol or benzyl alcohol, N-methylpyrrolidone, propylene carbonate, glycofurol, dimethylacetamide, 2-pyrrolidone, isopropylideneglycerol, or glycerolformal. The solvents can also be employed in mixtures or combinations. Water-based formulations are preferred and may, of course, comprise further solvents and cosolvents.

The liquid formulation may comprise as solvent apart from water or water-miscible substances also oils in the form of an emulsion. Mention may be made in this connection of vegetable, animal and synthetic oils such as cottonseed oil, sesame oil, soya oil, medium chain triglycerides of a chain length of $C_{12}$-$C_{18}$, propylene glycol octanoate decanoate or else paraffin.

The solvent (or solvent mixture) is normally present in concentrations of up to 98%, preferably up to 90%, particularly preferably up to 87%. The concentrations of the solvent are ordinarily over 65%, preferably over 75%, particularly preferably over 85%. The percentage data mean % (M/V).

The formulations according to the invention may also comprise cosolvents, specifically and preferably when the formulations comprise water; the cosolvents may improve the solubility of certain ingredients of the formulation. The cosolvents are normally employed in proportions of from 0.1 to 30%, preferably from 1 to 10% (percentage data in each case M/V). Examples of cosolvents which may be mentioned are: pharmaceutically acceptable alcohols, dimethyl sulphoxide, ethyl lactate, ethyl acetate, triacetin. Mixtures of the aforementioned solvents can also be employed as cosolvent. In some circumstances, individual cosolvents can also be employed as solvents. Normally, the cosolvents employed in the preparations according to the invention are only those which have not been already used as solvent or in the solvent mixture.

Preservatives may be present in the liquid formulation. Examples which may be mentioned of preservatives which can be used are: aliphatic alcohols such as benzyl alcohol, ethanol, n-butanol, phenol, cresols, chlorobutanol, para-hydroxybenzoic esters (especially the methyl and propyl esters), salts or the free acids of carboxylic acids such as sorbic acid, benzoic acid, lactic acid or propionic acid. Likewise the quaternary ammonium compounds such as, for example, benzalkonium chloride, benzethonium chloride or cetylpyridinium chloride. Preservatives are normally employed in proportions of from 0.001 to 5%, preferably from 0.01 to 4%. Where the preparations according to the invention already comprise in sufficient quantity a component which may serve as preservative (e.g. n-butanol), normally no additional proportion is added for preservation purposes. It is, however, where appropriate possible to add other preservatives also.

Depending on the nature of the formulation and administration form, the medicaments according to the invention may comprise further customary, pharmaceutically acceptable additives and excipients. Examples which may be mentioned are Antioxidants such as, for example, sulphites (Na sulphite, Na metabisulphite), organic sulphides (cystine, cysteine, cysteamine, methionine, thioglycerol, thioglycolic acid, thiolactic acid), phenols (tocopherols, as well as vitamin E and derivatives thereof, e.g. vitamin E TPGS (d-alpha-tocopheryl polyethylene glycol 1000 succinate)), butylhydroxyanisole, butylhydroxytoluene, octyl and dodecyl gallate), organic acids (ascorbic acid, citric acid, tartaric acid, lactic acid) and their salts and esters. Normally, 0.01-5, preferably 0.05-1, % are employed.

Wetting agents such as, for example, fatty acid salts, fatty alkyl sulphates, fatty alkylsulphonates, linear alkylbenzenesulphonates, fatty alkyl polyethylene glycol ether sulphates, fatty alkyl polyethylene glycol ethers, alkylphenol polyethylene glycol ethers, alkyl polyglycosides, fatty acid N-methylglucamides, polysorbates, sorbitan fatty acid esters and poloxamers. Normally 0.01-10%, preferably 0.1-5%, are employed.

Substances for isotonicity such as, for example, sodium chloride, glucose or glycerol. Normally 0.01-5%, preferably 0.1-1%, are employed.

Substances able to prevent particle formation; e.g. poloxamers, lecithins, polyvinylpyrrolidones, cosolvents, antioxidants such as, for example, sodium disulphite or complexing agents such as, for example, the sodium salt of editic acid. Normally 0.01-5%, preferably 0.05-1%, are employed.

The liquid formulations may comprise substances which improve local tolerability on administration. Examples which may be mentioned are: radical scavengers or antioxidants such as, for example, vitamin E, or vitamin C, butylhydroxyanisole, butylhydroxytoluene, cysteamine, cysteine, glutathione, thioglycol, thiolactic acid, sodium disulphide or else acetylcysteine. Complexing agents such as, for example, cyclodextrins (e.g. hydroxypropylcyclodextrin), sodium EDTA (ethylenediaminetetraacetic acid), polyvinylpyrrolidone, dexpanthenol, salts of fatty acids such as, for example, sodium caprylate, salts of multiply charged metal cations (e.g. $Me^{2+}$ or $Me^{3+}$), especially of the alkaline earth metals, amino acids and, of these, in particular arginine or lysine, poloxamers, poloxamines, solvents or cosolvents such as, for example, glycerol, polyethylene glycol, propylene glycol or dimethylacetamide, dextrans, creatine, creatinine, acids such as, for example, gluconolactonic acid, lactic acid, embonic acid, citric acid, tartaric acid, mucic acid or hyaluronic acid, lecithins with a phosphatidylcholine content of 70-100% from soya or egg white. Normally, 0.01-20%, preferably 0.1-10%, are employed.

Pharmaceutically acceptable colorants such as, for example, iron oxides, carotenoids, etc. Normally, 0.01-10%, preferably 0.1-5% are employed.

The pH of the liquid preparations is 2-11, preferably 3-8 and particularly preferably 4-7. The pH is adjusted where appropriate by adding pharmaceutically acceptable acids or bases. If the preparations comprise a pharmacologically active phosphonic acid, a base is preferably added to adjust the pH values indicated above.

Examples of bases which can be used are: alkali metal or alkaline earth metal hydroxides (e.g. NaOH, KOH; where appropriate in the form of their aqueous solutions: sodium hydroxide solution, potassium hydroxide solution), or basic phosphates, e.g. sodium phosphate, sodium hydrogenphosphate, basic amino acids such as, for example, lysine, arginine, histidine, ornithine, citrulline, hydroxylysine, choline, meglumine, ethanolamines such as triethanolamine or else buffers (tris(hydroxymethyl)aminomethane, cyclohexylamino-1-propanesulphonic acid). The base preferably employed is: NaOH, KOH or arginine; NaOH is particularly preferred, where appropriate as aqueous sodium hydroxide solution.

Examples of acids which can be used are: inorganic acids such as, for example, hydrochloric acid, sulphuric acid, phosphoric acid or organic acids such as, for example, methanesulphonic acid, formic acid, acetic acid, propionic acid, lactic acid, malonic acid, adipic acid, tartaric acid, oxalic acid, fumaric acid, malic acid, citric acid, succinic acid, aspartic acid, glutamic acid, gluconic acid, glucuronic acid, galacturonic acid, glutaric acid, lactobionic acid, mandelic acid, salicylic acid, ascorbic acid, benzoic acid, maleic acid, citric acid, octanoic acid, linoleic acid, linolenic acid.

The required amount of acid or base is governed by the desired pH. Normally the acid or base is used in a proportion of from 0.0001 to 20%, preferably 0.001 to 10%.

The acids can be used with a proportion of from 0.0001 to 20%, preferably 0.01 to 10%.

The medicaments of the invention can be manufactured by dispersing the vitamin in the solvent. The vitamin can be dispersed directly or, for quantitative conversion, by using a stock solution in the solvent. Apart from the actual solvent it is possible also to use other solvents as stock solution. Where appropriate, the pharmacologically acceptable phosphonic acid derivative is likewise dispersed in the solvent. The butanol or mixtures of butanol and solvent are added. Cosolvents and further ingredients such as, for example, antioxidants may have been added to the solvent or can be admixed later. The pH is adjusted, e.g. with a base. To protect the vitamin $B_{12}$, parts of the manufacture and filling of the solutions can take place under a protective gas atmosphere, e.g. introducing nitrogen gas.

Alternatively, butanol and, where appropriate, also the phamacologically acceptable phosphonic acid derivative can initially be dissolved in the solvent and then the vitamin $B_{12}$ can be added.

The pharmaceutical preparations according to the invention are generally suitable for use in humans and animals. They are preferably employed in animal management and animal breeding among productive and breeding livestock, zoo, laboratory and experimental animals, and pets.

The productive and breeding livestock include mammals such as, for example, cattle, horses, sheep, pigs, goats, camels, water buffaloes, donkeys, rabbits, fallow deer, reindeer, fur-bearing animals such as, for example, mink, chinchilla, racoon, and birds such as, for example, quail, chicken, geese, turkeys, ducks, pigeons and bird species for keeping at home and in zoos.

Laboratory and experimental animals include mice, rats, guinea pigs, golden hamsters, rabbits, monkeys, dogs and cats.

Pets include rabbits, hamsters, rats, guinea pigs, mice, horses, reptiles, appropriate bird species, dogs and cats.

Mention may also be made of fish, specifically of productive, breeding, aquarium and ornamental fish of all ages which live in fresh water and salt water.

In the case of pets, the preparations according to the invention are preferably employed for horses, rabbits, cats and dogs. They are particularly suitable for use in cats and dogs.

In the case of productive livestock, the preparations according to the invention are preferably employed for cattle, sheep, pigs, goats, turkeys and chickens. Particularly preferred productive livestock are cattle and pigs.

Use is possible either prophylactically, metaphylactically or therapeutically.

Liquid formulations according to the invention are preferably emulsions or, in particular, solutions.

The formulations described herein can be supplied to the target organism (human or animal) in various ways. They can be administered for example parenterally, in particular by injection (e.g. subcutaneous, intramuscular, intravenous, intramammary, intraperitoneal), dermally, orally, rectally, vaginally or nasally, with preference for oral and parenteral administration—especially by injection. Parenteral administration by injection is particularly preferred.

The use with the stated substances leads to medicaments having good stability of vitamin $B_{12}$, especially to light.

EXAMPLES

The formulations of the following examples are produced by mixing or dissolving the stated ingredients in water for injections or distilled water or demineralized water. To introduce the cyanocobalamin quantitatively into the main mixture it is advisable to use a stock solution. This is not, however, obligatory. The pH of the solutions can be adjusted by adding acids or bases. The solutions are produced and filled under nitrogen protection. The solutions for injection are sterilized by filtration and transferred into suitable containers. Percentage data in percent by weight are based on the total volume of the finished product (M/V).

Example 1

10% Butaphosphan
0.005% cyanocobalamin (vitamin $B_{12}$)
3.0% n-butanol
quantum satis sodium hydroxide
ad 100% water for injections
0.0005 g of vitamin $B_{12}$ is dissolved in a partial quantity of water for injections by heating. 1.0 g of butaphosphan and 0.3 g of n-butanol are dissolved in water for injections and added to the stock solution with cyanocobalamin. The pH is adjusted with sodium hydroxide to 5.6 (+/−0.2), and the final weight is adjusted to 10 ml with water for injections.

Example 2

0.005% Cyanocobalamin (vitamin $B_{12}$)
3.0% n-butanol
quantum satis sodium hydroxide
ad 100% water for injections
0.0010 g of vitamin $B_{12}$ is dissolved in a partial quantity of water for injections by heating. 0.6 g of n-butanol are dissolved in water for injections and added to the stock solution with cyanocobalamin. The pH is adjusted with sodium hydroxide to 5.6 (+/−0.2), and the final weight is adjusted to 20 ml with water for injections.

Example 3

10% Butaphosphan
0.005% cyanocobalamin (vitamin $B_{12}$)
2.0% n-butanol
quantum satis sodium hydroxide
ad 100% water for injections
0.0025 g of vitamin $B_{12}$ is dissolved in a partial quantity of water for injections by heating. 5.0 g of butaphosphan and 1.0 g of n-butanol are dissolved in water for injections and added to the stock solution with cyanocobalamin. The pH is adjusted with sodium hydroxide to 5.6 (+/−0.2), and the final weight is adjusted to 50 ml with water for injections.

Example 4

20% Butaphosphan
0.010% cyanocobalamin (vitamin $B_{12}$)
3.0% n-butanol
quantum satis potassium hydroxide
ad 100% water for injections
0.0010 g of vitamin $B_{12}$ is dissolved in a partial quantity of water for injections by heating. 2.0 g of butaphosphan and 0.3 g of n-butanol are dissolved in water for injections and added to the stock solution with cyanocobalamin. The pH is adjusted to 5.6 (+/−0.2), and the final weight is adjusted to 10 ml with water for injections.

Example 5

10% Butaphosphan
0.005% cyanocobalamin (vitamin $B_{12}$)
4.0% n-butanol
quantum satis sodium hydroxide
ad 100% water for injections
0.005 g of vitamin $B_{12}$ is dissolved in a partial quantity of water for injections by heating. 10.0 g of butaphosphan and 4.0 g of n-butanol are dissolved in water for injections and added to the stock solution with cyanocobalamin. The pH is adjusted with sodium hydroxide to 5.6 (+/−0.2), and the final weight is adjusted to 100 ml with water for injections.

Example 6

15% Butaphosphan
0.0075% cyanocobalamin (vitamin $B_{12}$)
3.0% n-butanol
quantum satis meglumine
ad 100% water for injections
0.00075 g of vitamin $B_{12}$ is dissolved in a partial quantity of water for injections by heating. 1.5 g of butaphosphan and 0.3 g of n-butanol are dissolved in water for injections and added to the stock solution with cyanocobalamin. The pH is adjusted with meglumine to 5.6 (+/−0.2), and the final weight is adjusted to 10 ml with water for injections.

Example 7

30% Butaphosphan
0.015% cyanocobalamin (vitamin $B_{12}$)
3.0% n-butanol
quantum satis arginine
ad 100% water for injections
0.0015 g of vitamin $B_{12}$ is dissolved in a partial quantity of water for injections by heating. 3.0 g of butaphosphan and 0.3 g of n-butanol are dissolved in water for injections and added to the stock solution with cyanocobalamin. The pH is adjusted with arginine to 5.6 (+/−0.2), and the final weight is adjusted to 10 ml with water for injections.

Example 8

0.010% Cyanocobalamin (vitamin $B_{12}$)
3.0% n-butanol
quantum satis arginine
ad 100% water for injections
0.0010 g of vitamin $B_{12}$ is dissolved in a partial quantity of water for injections by heating. 0.3 g of n-butanol is mixed with water for injections and added to the stock solution with cyanocobalamin. The pH is adjusted with arginine to 5.6 (+/−0.2), and the final weight is adjusted to 10 ml with water for injections.

Stability to Light

The formulations described herein have shown an improved photostability compared with other formulations. Selected examples thereof are listed in the following table. The results are depicted once again graphically in FIG. 1.

TABLE 1

Comparison of the photostabilities of a formulation without n-butanol (A) with a formulation with n-butanol (B).

| | Initial vitamin $B_{12}$ content in mg/100 ml | Vitamin $B_{12}$ content in mg/100 ml after illumination for 3 h |
|---|---|---|
| Formulation A | 5.50 | 3.99 |
| Formulation B according to Example 1 | 5.53 | 4.91 |

What is claimed is:

1. A photostable vitamin $B_{12}$ formulation comprising:
   0.001 to 0.01% m/V vitamin $B_{12}$;
   butaphosphan;
   0.5 to 7% n-butanol m/V; and
   water,
   wherein the pH of the formulation is from about 4 to about 7.
2. The formulation of claim 1 comprising from 1 to 5% m/V n-butanol.
3. The formulation of claim 1 comprising from 2 to 4% m/V n-butanol.
4. The formulation of claim 1 comprising from 0.005 to 0.01% m/V vitamin $B_{12}$.
5. The formulation of claim 1 comprising from 1 to 30% m/V butaphosphan.
6. The formulation of claim 1 comprising from 5 to 20% m/V butaphosphan.
7. The formulation of claim 2 comprising from 5 to 20% m/V butaphosphan.
8. The formulation of claim 1, wherein the pH of the formulation is 5.6±0.2.
9. The formulation of claim 7, wherein the pH of the formulation is 5.6±0.2.
10. The formulation of claim 1, wherein the vitamin $B_{12}$ is cyanocobalamin.
11. The formulation of claim 7, wherein the vitamin $B_{12}$ is cyanocobalamin.
12. The formulation of claim 1 further comprising a base.
13. The formulation of claim 11 further comprising a base.
14. The formulation of claim 13, wherein the base comprises sodium hydroxide.
15. The formulation of claim 1, wherein water constitutes over 75% m/V of the formulation.
16. The formulation of claim 11, wherein water constitutes over 75% m/V of the formulation.
17. The formulation of claim 1 further comprising a cosolvent.
18. The formulation of claim 1 further comprising an antioxidant, wetting agent, or combinations thereof.

* * * * *